US012806096B2

(12) United States Patent
Sidhu et al.

(10) Patent No.: US 12,806,096 B2
(45) **Date of Patent: *Nov. 24, 2026**

(54) TECHNIQUES FOR NOTIFYING PERSONS WITHIN A VICINITY OF A PATIENT SUPPORT APPARATUS OF A REMOTE CONTROL FUNCTION

(71) Applicant: Stryker Corporation, Portage, MI (US)

(72) Inventors: Anuj Sidhu, Kalamazoo, MI (US); Alexander Bodurka, Portage, MI (US); Akash Agrawal, Maharashtra (IN); Brajesh Kumar, Alirgarh (IN); Sachin Pachauri, Hathras (IN); Chandra Bhanu Vats, Laxmisagar (IN)

(73) Assignee: Stryker Corporation, Portage, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/097,049

(22) Filed: Apr. 1, 2025

(65) Prior Publication Data

US 2025/0228722 A1 Jul. 17, 2025

Related U.S. Application Data

(63) Continuation of application No. 17/125,361, filed on Dec. 17, 2020, now Pat. No. 12,285,373, which is a (Continued)

(51) Int. Cl.

*A61G 7/05* (2006.01)
*A61B 5/00* (2006.01)

(Continued)

(52) U.S. Cl.

CPC ............ *A61G 7/0524* (2016.11); *A61G 7/015* (2013.01); *A61G 7/018* (2013.01); *A61G 7/0506* (2013.01);

(Continued)

(58) Field of Classification Search

CPC ...... A61G 7/015; A61G 7/018; A61G 7/0506; A61G 7/0524; A61G 7/0528;

(Continued)

(56) References Cited

U.S. PATENT DOCUMENTS

| | | | |
|---|---|---|---|
| 5,699,038 A | 12/1997 | Ulrich et al. |
| 5,838,223 A | 11/1998 | Gallant et al. |

(Continued)

FOREIGN PATENT DOCUMENTS

| | | |
|---|---|---|
| CA | 2529091 A1 | 12/2003 |
| WO | 0185085 A2 | 11/2001 |

OTHER PUBLICATIONS

Hill-Rom, "Centrella Smart+Bed Brochure" 2017, 11 pages.
Youtube "Tesla Charging Snake Video", Aug. 6, 2015, https://www.youtube.com/watch?v=ut3sELMOyTM, 3 pages.

*Primary Examiner* — David R Hare
(74) *Attorney, Agent, or Firm* — Howard & Howard Attorneys PLLC

(57) ABSTRACT

A patient support apparatus and a method of notifying persons within a vicinity of the patient support apparatus are disclosed. The patient support apparatus includes a patient support structure for supporting a patient, an actuator for moving the patient, a notification system, and a controller coupled to the notification system and the actuator. The controller receives a selection of a remote control function via a communication network, generates a notification in response to receiving the selection of the remote control function, and transmits an output signal to the actuator based on the selection of the remote control function. The notification system executes the notification prior to the controller transmitting the output signal to the actuator.

20 Claims, 5 Drawing Sheets

Related U.S. Application Data continuation of application No. 16/211,925, filed on Dec. 6, 2018, now Pat. No. 10,905,611.

(60) Provisional application No. 62/609,801, filed on Dec. 22, 2017.

(51) Int. Cl.
*A61G 7/015* (2006.01)
*A61G 7/018* (2006.01)
*A61G 7/10* (2006.01)

(52) U.S. Cl.
CPC .......... *A61G 7/1065* (2013.01); *A61B 5/6892* (2013.01); *A61B 2562/0252* (2013.01); *A61G 7/0528* (2016.11); *A61G 7/1046* (2013.01); *A61G 7/1067* (2013.01); *A61G 2203/32* (2013.01)

(58) Field of Classification Search
CPC .. A61G 7/1046; A61G 7/1065; A61G 7/1067; A61G 2203/32; A61B 5/01; A61B 5/021; A61B 5/024; A61B 5/6892; A61B 2562/0252; G16H 40/60
USPC ............................................................... 5/425
See application file for complete search history.

(56) References Cited

U.S. PATENT DOCUMENTS

| | | | |
|---|---|---|---|
| 6,802,385 B2 | 10/2004 | Pyntikov et al. | |
| 7,109,848 B2 | 9/2006 | Schybergson | |
| 7,319,386 B2 | 1/2008 | Collins, Jr. et al. | |
| 7,480,951 B2 | 1/2009 | Weismiller et al. | |
| 7,557,689 B2 | 7/2009 | Seddigh et al. | |
| 7,808,391 B2 | 10/2010 | Nixon | |
| 7,852,208 B2 | 12/2010 | Collins, Jr. et al. | |
| 7,941,881 B2 | 5/2011 | Hayes et al. | |
| 7,958,201 B2 | 6/2011 | Lindsay | |
| 8,121,856 B2 | 2/2012 | Huster et al. | |
| 8,266,742 B2 | 9/2012 | Andrienko | |
| 8,284,047 B2 | 10/2012 | Collins, Jr. et al. | |
| 8,618,918 B2 | 12/2013 | Tallent et al. | |
| 8,856,383 B2 | 10/2014 | Beninato et al. | |
| 9,056,556 B1 | 6/2015 | Hyde et al. | |
| 9,079,505 B1 | 7/2015 | Hyde et al. | |
| 9,094,723 B2 | 7/2015 | Reams | |
| 9,185,202 B2 | 11/2015 | Herbst et al. | |
| 9,204,823 B2 | 12/2015 | Derenne et al. | |
| 9,305,450 B2 | 4/2016 | Halverson et al. | |
| 9,307,033 B1 | 4/2016 | Meschkat | |
| 9,513,899 B2 | 12/2016 | Collins, Jr. et al. | |
| 9,539,155 B2 | 1/2017 | Johannigman et al. | |
| 9,539,156 B2 | 1/2017 | Lemire et al. | |
| 9,734,293 B2 | 8/2017 | Collins, Jr. et al. | |
| 9,833,194 B2 | 12/2017 | Hayes et al. | |
| 10,004,651 B2 | 6/2018 | DeLuca et al. | |
| 10,905,611 B2 * | 2/2021 | Sidhu | A61G 7/015 |
| 11,074,802 B2 | 7/2021 | Wong et al. | |
| 12,285,373 B2 * | 4/2025 | Sidhu | A61G 7/0524 |
| 2002/0014951 A1 * | 2/2002 | Kramer | G16H 10/60 340/286.07 |
| 2004/0030531 A1 | 2/2004 | Miller et al. | |
| 2005/0113996 A1 | 5/2005 | Pillar et al. | |
| 2006/0235283 A1 | 10/2006 | Vinarov et al. | |
| 2006/0277683 A1 * | 12/2006 | Lamire | A61G 7/0507 5/425 |
| 2007/0010719 A1 | 1/2007 | Huster et al. | |
| 2007/0174964 A1 | 8/2007 | Lemire et al. | |
| 2007/0210917 A1 | 9/2007 | Collins et al. | |
| 2009/0088924 A1 | 4/2009 | Coffee et al. | |
| 2009/0096615 A1 | 4/2009 | Reeder et al. | |
| 2011/0074571 A1 | 3/2011 | Collins, Jr. et al. | |
| 2011/0112442 A1 | 5/2011 | Meger et al. | |
| 2011/0301440 A1 | 12/2011 | Riley et al. | |
| 2012/0259245 A1 * | 10/2012 | Receveur | A61G 7/0514 5/616 |
| 2014/0094997 A1 | 4/2014 | Hyde et al. | |
| 2014/0259414 A1 | 9/2014 | Hayes et al. | |
| 2014/0297327 A1 | 10/2014 | Heil et al. | |
| 2015/0135440 A1 | 5/2015 | Chiacchira et al. | |
| 2015/0239365 A1 | 8/2015 | Hyde et al. | |
| 2015/0281659 A1 | 10/2015 | Hood et al. | |
| 2016/0199240 A1 | 7/2016 | Newkirk et al. | |
| 2016/0259906 A1 | 9/2016 | Iucha et al. | |
| 2016/0338891 A1 | 11/2016 | Agdeppa et al. | |
| 2016/0350489 A1 | 12/2016 | Ribble et al. | |
| 2016/0367420 A1 | 12/2016 | Zerhusen et al. | |
| 2017/0011181 A1 | 1/2017 | McNeely et al. | |
| 2017/0124844 A1 | 5/2017 | Huster et al. | |
| 2018/0110445 A1 | 4/2018 | Bhimavarapu et al. | |
| 2018/0214091 A1 | 8/2018 | Baker et al. | |
| 2018/0303687 A1 | 10/2018 | Moreno et al. | |
| 2019/0192368 A1 | 6/2019 | Sidhu et al. | |
| 2021/0106478 A1 | 4/2021 | Sidhu et al. | |

* cited by examiner

TECHNIQUES FOR NOTIFYING PERSONS WITHIN A VICINITY OF A PATIENT SUPPORT APPARATUS OF A REMOTE CONTROL FUNCTION

CROSS-REFERENCE TO RELATED APPLICATIONS

The subject patent application is a Continuation of U.S. patent application Ser. No. 17/125,361 filed on Dec. 17, 2020, which is a Continuation of U.S. patent application Ser. No. 16/211,925 filed on Dec. 6, 2018 and issued as U.S. Pat. No. 10,905,611 on Feb. 2, 2021, which claims priority to and all the benefits of U.S. Provisional Patent Application No. 62/609,801 filed on Dec. 22, 2017, the disclosures of each of which are hereby incorporated by reference in their entirety.

BACKGROUND

Actuators are commonly used on medical devices for various purposes. Such medical devices may include, for example, patient support apparatuses, such as hospital beds, stretchers, cots, tables, wheelchairs, recliners, and chairs for patient care. Other medical devices may include equipment such as lights, televisions, temperature management systems, respirators, IV lines, surgical tools, and heart rate monitors that may be used in medical procedures or in the provision of medical services to patients. For example, a patient support apparatus may be equipped with a lift assembly that uses actuators to lift a patient resting on a patient support surface to a desired height. In another example, an actuator may be used to manipulate angular positioning of portions of the patient support surface, such as the fowler, etc.

Typically, these actuators are controlled by a controller, which may, in some cases, accept remote control functions for controlling the actuators. However, such a configuration falls short in many ways. For example, remote control functions may cause unnecessary anxiety in a patient resting on a patient support apparatus. Furthermore, if a patient exhibits anxious behavior, the patient support apparatus may be unable to adapt due to a remote nature of the remote control function. In other instances, remote control functions may create safety issues not only for patients resting on the patient support surface, but also for persons within a vicinity of the patient support apparatus. As such, there are opportunities to address at least the aforementioned problems.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Referring to the Figures, wherein like numerals indicate like or corresponding parts throughout the several views, techniques for notifying persons within a vicinity of a patient support apparatus of a remote control function are provided.

Figure 1:
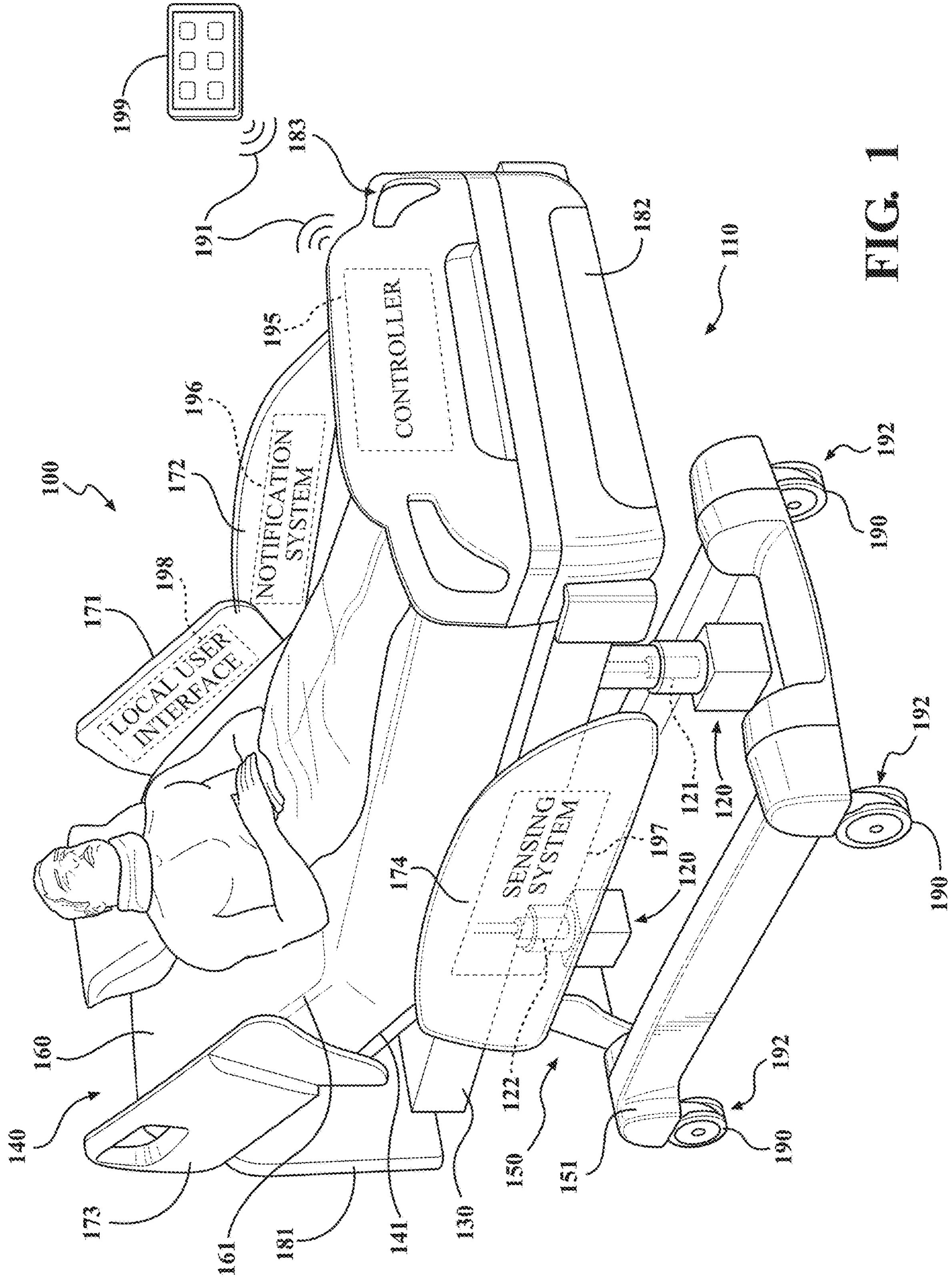
FIG. 1 is a perspective view of a patient support apparatus and a remote device.

Referring to FIG. 1, an embodiment of the patient support apparatus 100 is shown for supporting a patient in a health care setting. The patient support apparatus 100 illustrated in FIG. 1 includes a hospital bed. However, in other embodiments, the patient support apparatus 100 may include a stretcher, a cot, a table, a wheelchair, a recliner, a chair for patient care, or any other similar apparatus utilized in the care of a patient.

A support structure 110 provides support for the patient. The support structure 110 illustrated in FIG. 1 includes a base 150 and a support frame 130. The base 150 includes a base frame 151. The support frame 130 is spaced above the base frame 151 in FIG. 1. The support structure 110 also includes a patient support deck 140 disposed on the support frame 130. The patient support deck 140 includes several sections, some of which are capable of articulating relative to the support frame 130, such as a back section, a seat section, a thigh section, and a foot section. The patient support deck 140 provides a patient support surface 141 upon which the patient is supported.

A mattress 160 may be disposed on the patient support deck 140 during use. The mattress 160 includes a secondary patient support surface 161 upon which the patient is supported. In addition, the mattress 160 may be omitted in certain embodiments, such that the patient rests directly on the patient support surface 141.

The base 150, support frame 130, patient support deck 140, and patient support surface 141 each have a head end and a foot end corresponding to a designated placement of the patient's head and feet on the patient support apparatus 100. The construction of the support structure 110 may take on any suitable design, and is not limited to that specifically set forth above.

Side rails 171, 172, 173, 174 are coupled to the support frame 130 or the patient support deck 140 and are thereby supported by the base 150. A first side rail 171 is positioned at a left head end of the patient support deck 140. A second side rail 172 is positioned at a left foot end of the support frame 130. A third side rail 173 is positioned at a right head end of the patient support deck 140. A fourth side rail 174 is positioned at a left foot end of the support frame 130. If the patient support apparatus 100 is a stretcher or a cot, there may be fewer side rails. The side rails 171, 172, 173, 174 are movable to a raised position in which they block ingress and egress into and out of the patient support apparatus 100, one or more intermediate positions, and a lowered position in which the side rails 171, 172, 173, 174 are not an obstacle to such ingress and egress. In still other configurations, the patient support apparatus 100 may not include any side rails.

A headboard 181 and a footboard 182 are coupled to the support frame 130. In other embodiments, when the headboard 181 and footboard 182 are included, the headboard 181 and footboard 182 may be coupled to other locations on the patient support apparatus 100, such as the base 150. In still other embodiments, the patient support apparatus 100 does not include the headboard 181 and/or the footboard 182.

Caregiver interfaces 183, such as handles, are shown integrated into the footboard 182 and side rails 171, 172, 173, 174 to facilitate movement of the patient support apparatus 100 over floor surfaces. Additional caregiver interfaces 183 may be integrated into the headboard 181 and/or other components of the patient support apparatus 100. The caregiver interfaces 183 are graspable by a caregiver to manipulate the patient support apparatus 100 for movement.

Wheels 190 are coupled to the base 150 to facilitate transport over the floor surfaces. The wheels 190 are arranged in each of four quadrants of the base 150 adjacent to corners of the base 150. In the embodiment shown, the wheels 190 are caster wheels able to rotate and swivel relative to the support structure 110 during transport. Each of the wheels 190 forms part of a caster assembly 192. Each caster assembly 192 is mounted to the base 150. It should be understood that various configurations of the caster assemblies 192 are contemplated. In addition, in some embodiments, the wheels 190 are not caster wheels and may be non-steerable, steerable, non-powered, powered, or combinations thereof. Additional wheels are also contemplated. For example, the patient support apparatus 100 may include four non-powered, non-steerable wheels, along with one or more powered wheels. In some cases, the patient support apparatus 100 may not include any wheels.

In other embodiments, one or more auxiliary wheels (powered or non-powered), which are movable between stowed positions and deployed positions, may be coupled to the support structure 110. In some cases, when these auxiliary wheels are located between caster assemblies 192 and contact the floor surface in the deployed position, they cause two of the caster assemblies 192 to be lifted off the floor surface thereby shortening a wheel base of the patient support apparatus 100. A fifth wheel may also be arranged substantially in a center of the base 150.

As shown in FIG. 1, the system 10 may include an actuatable device 120 and actuators 121, 122. The actuators 121, 122 may be further defined as being capable of moving the actuatable device 120. The actuators 121, 122 may be coupled to the support structure 110 to move the patient when the patient is disposed on the patient support structure 110. In the embodiment of the patient support apparatus 100 shown in FIG. 1, the patient support apparatus 100 includes two actuators 121, 122. However, it is to be noted that the patient support apparatus 100 may include any suitable number of actuators 121, 122. Furthermore, any of the techniques described herein can utilize any number of actuators 121, 122 individually or in combination.

The actuators 121, 122 should be broadly understood as a type of motor or device that is capable of moving or controlling a mechanism or a system. For example, some suitable, non-limiting examples of the actuators 121, 122 are mechanical, hydraulic, pneumatic, electric, thermal, or magnetic actuators. The actuators 121, 122 may also include motors, such as a rotational or linear motor. In a further example, the actuators 121, 122 may include an inflation actuator. In sum, it should be understood that any type of actuator can be used in certain applications.

As described above, the actuators 121, 122 may be further defined as being capable of moving an actuatable device 120. These actuatable devices 120 are not particularly limited, and may include any device or system that includes one or more actuators 121, 122. In certain embodiments, the actuatable device 120 is one that, when actuated, results in a change of position of the patient support surfaces 141, 161 of the patient support structure 110. This change in position of one or more patient support surfaces 141, 161 when the patient occupies the patient support apparatus 100, results in a change in the position of one or more portions of the patient's body.

More specifically, in situations where a patient occupies the patient support apparatus 100, i.e., contacts one or more patient support surfaces 141, 161, operation of each of the actuatable devices 120 results in movement of one or more portions of the patient in one or more dimensions relative to a static surface, such as relative to a floor of a hospital. Examples of such movement include, but are not limited to: forward and reverse movement of the patient by virtue of movement of the patient support structure 110 along a floor; raising and lowering movement of the patient by virtue of movement of the patient support structure 110 upward and downwards relative to the floor; angular movement by virtue of changing the angle of at least a portion of the patient support structure 110 relative to a floor; rotation of the patient along a longitudinal axis of the patient support structure 110 (while the patient support apparatus 100 remains stationary relative to the floor); or various combinations of those types of movement.

Without limitation, the actuatable devices 120 that result in the change of the position of one or more patient support surfaces 141, 161 of the patient support structure 110 may include a coordinated motion device, a patient raising device, a patient turning device, a patient centering device, a patient ingress/egress device, a lift device, a fowler adjustment device, a gatch adjustment device, and a transport device.

It is also contemplated that the actuatable device 120 may be of the type that does not result in a change of position, orientation, and/or elevation of the patient support surfaces 141, 161. These "non-position actuatable devices" may include, but are not limited to, patient comfort devices, such as entertainment devices, lighting devices, a temperature device, a humidity device, and an aromatherapy device, as well as patient therapy devices, such as vibration therapy devices, percussion therapy devices, compression therapy devices, patient warming devices, and electrical stimulation devices. The rate of operation of these non-position actuatable devices may also be controlled by changing the frequency, tempo, rate of temperature change, rate of humidity change, intensity of therapy, etc. of the devices.

In FIG. 1, the patient support apparatus 100 also includes a notification system 196, which executes a notification to notify a person within a vicinity of the patient support apparatus 100. In FIG. 1, the notification system 196 is disposed within the second side rail 172. However, in other embodiments, the notification system 196 may be disposed on or within the headboard 181, the footboard 182, any of the side rails 171, 172, 173, 174, the caregiver interfaces 183, a movable pendant or computing device, or any other suitable component of the patient support apparatus 100. In still other embodiments, the notifications system 196 may be separated from the patient support apparatus 100, but included in a hospital room of the patient. For example, the notification system 196 may be mounted to a ceiling of the room, a support structure of the room, or a wall of the room.

The notification system 196 may include a visual alert system, an audio alert system, a tactile alert system, or combinations thereof. For example, the notification system 196 may include a light assembly, an electronic display, an audible alarm device, a vibrating device, or any other suitable notification system for notifying the person within the vicinity of the patient support apparatus 100. Accordingly the notification system 196 may illuminate lights of the light assembly in various patterns, sequences, and color combinations; activate the audible alarm device using various frequencies, amplitudes, pitches, patterns, and tones; vibrate the vibrating device using various frequencies, patterns, and intensities such that the patient feels the resulting vibrations; and/or display text or graphic displays on the electronic display to indicate a type of remote control function, a characteristic of the remote control function, and/or one or more sensations that may accompany the remote control function.

Furthermore, the person within the vicinity of the patient support apparatus 100 may be any one of a patient, a caregiver, a family member, a hospital staff member, or any other suitable person. Alternatively, depending on a configuration of the notification device, a plurality of persons within the vicinity of the patient support apparatus 100 may be notified by the notification system 196.

Additionally, the patient support apparatus 100 may include a local user interface 198. In FIG. 1, the local user interface 198 is illustrated as being disposed within the first side rail 171. However, in other embodiments, the local user interface 198 may be disposed on or within the headboard 181, the footboard 182, any of the side rails 171, 172, 173, 174, the caregiver interfaces 183, or any other suitable component of the patient support apparatus 100. The local user interface 198 may include a switch, a button, a latch, a touchscreen display, a microphone, or combinations thereof for receiving an input from persons within the vicinity of the patient support apparatus 100.

The patient support apparatus 100 may also include a sensing system 197. In FIG. 1, the sensing system 197 is illustrated as being disposed within the fourth side rail 174. However, in other embodiments, the sensing system 197 may be disposed on or within the headboard 181, the footboard 182, any of the side rails 171, 172, 173, 174, the caregiver interfaces 183, or any other suitable component of the patient support apparatus 100.

The patient support apparatus 100, as shown in FIG. 1, also includes a controller 195. In FIG. 1, the controller 195 is illustrated as being disposed within the footboard 182. However, in other embodiments, the controller 195 may be disposed on or within the headboard 181, the side rails 171, 172, 173, 174, the caregiver interfaces 183, or any other suitable component of the patient support apparatus 100.

As shown in FIG. 1, the controller 195 may communication with a remote device 199 via a communication network 191. The remote device 199 may be any suitable remote device. For example, the remote device 199 may be any one of a cellular phone, a desktop computer, a nurse call station, a tablet, a laptop, a wearable remote device, or any other suitable remote device 199. Similarly, the communication network 191 may be any suitable communication network. The communication network 191 may include any one of Bluetooth, WiFi, Infrared, ZigBee, radio waves, or any other suitable communication network. In some embodiments, the communication network 191 may be implemented using a networking device such as a gateway device, a router, or a repeater.

Figure 2:
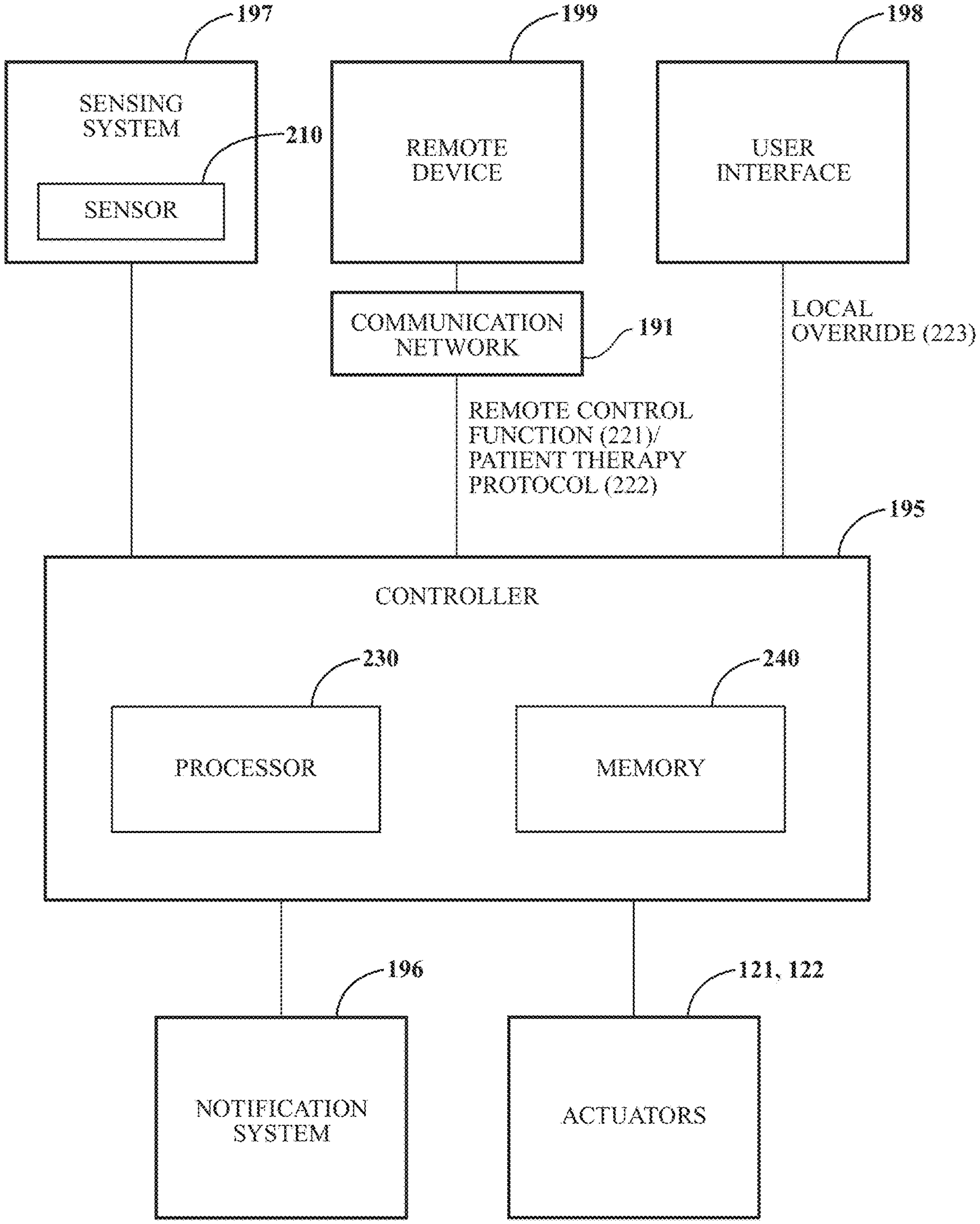
FIG. 2 is a block diagram illustrating a controller of the patient support apparatus, a notification system of the patient support apparatus, and a sensing system of the patient support apparatus.

FIG. 2 is a block diagram illustrating a configuration of the controller 195. As shown, the controller 195 includes a processor 230 and a memory 240. In FIG. 2, the controller 195 may be coupled to the notification system 196. The controller 195 may generate a notification, which the notification system 196 executes. Also shown in FIG. 2, the controller 195 may be coupled to the remote device 199 via the communication network 191 and may receive a selection of a remote control function 221 from the remote device 199 via the communication network 191. Furthermore, the controller 195 may be coupled to the actuators 121, 122 and may transmit an output signal to the actuators 121, 122 based on the selected remote control function 221.

Figure 3:
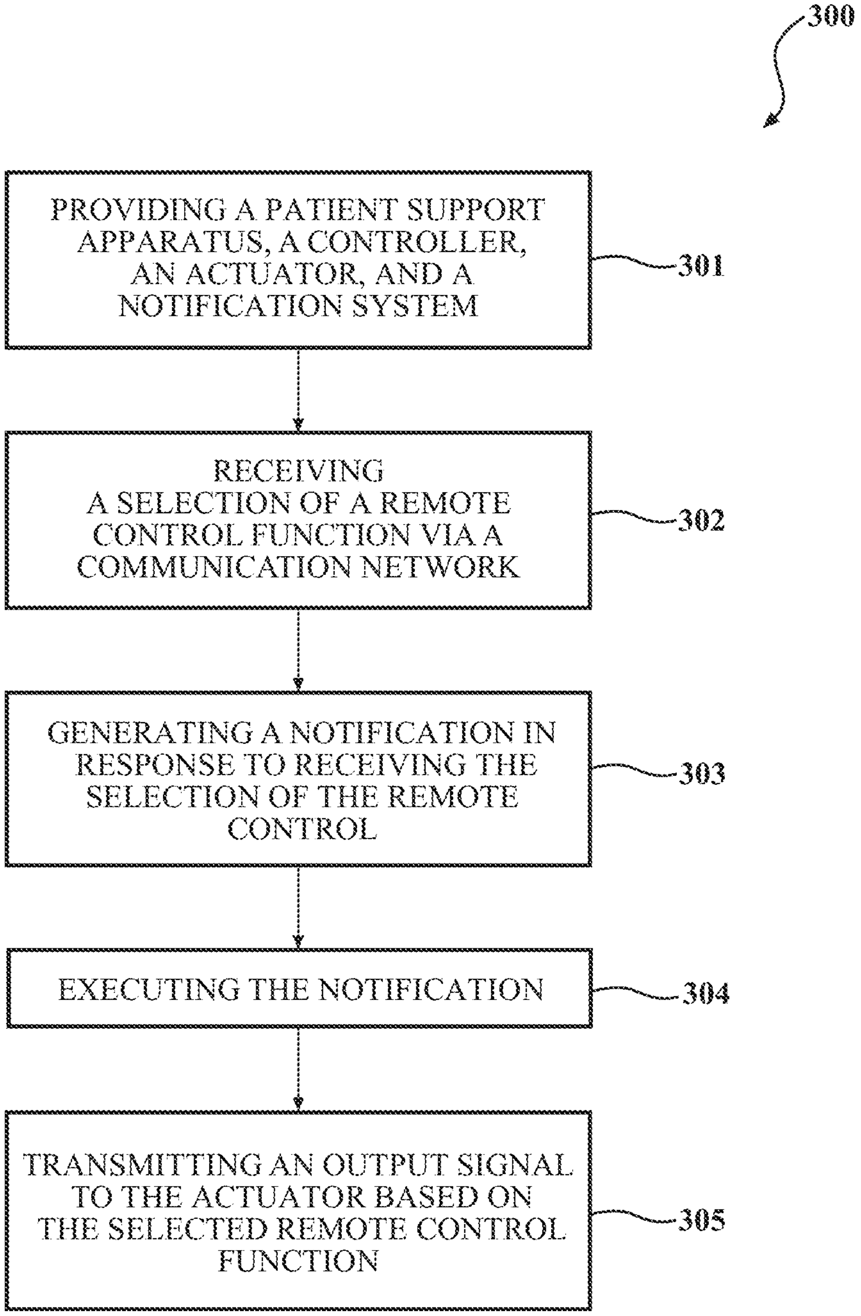
FIG. 3 is a flowchart illustrating a method of notifying persons within a vicinity of the patient support apparatus of a selected remote control function.

To further aid in understanding a configuration of the controller 195, FIG. 3 provides a flowchart illustrating a method of notifying persons within the vicinity of the patient support apparatus 100 of the selected remote control function 221. As shown, the method includes a step 301 of providing the patient support apparatus 100, the controller 195, the actuator 121, and the notification system 196. The method also includes a step 302 of receiving the selection of the remote control function 221 via the communication network; a step 303 of generating the notification in response to receiving the selection of the remote control; a step 304 of executing the notification; and a step 305 of transmitting the output signal to the actuators 121, 122 based on the selected remote control function 221. It should be noted that step 304 occurs prior to step 305. As such, persons within the vicinity of the patient support apparatus 100 may be notified of the selected remote control function 221 prior to its execution.

The remote control function 221 received by the controller 195 may be categorized as a non-patient remote control function or a patient remote control function. The remote control function 221 is categorized as a patient remote control function if the remote control function 221 causes movement of the patient support apparatus 100, causes movement of one or more actuatable devices 120 that are configured to move a patient or contact a patient, or could result in a change of state of the patient support apparatus 100 that could have adverse consequences for the patient. For example, a patient remote control function may cause the actuator 121, 122 to lift the side rails 171, 172, 173, 174, apply a brake of the patient support apparatus 100, lift the patient support deck 140, or incline the back section (i.e., the head end) of the patient support deck 140. In contrast, a non-patient remote control function does not cause movement of the patient support apparatus 100. For example, a non-patient remote control function may cause the controller 195 to activate a speaker of the patient support apparatus 100 to play music, one or more lights of the patient support apparatus 100, or other components of the patient support apparatus 100 which are unrelated to movement.

The notification generated during step 303 of the method may vary based on the selection of the remote control function 221. For example, a notification generated in response to a patient remote control function may differ from a notification generated in response to a non-patient remote control function. In one such embodiment, the notification system 196 may activate a light assembly of red warning lights in response to the patient remote control function and illuminate a green validation light in response to a non-patient remote control function. In another embodiment, the notification system 196 may activate the electronic display in response to the patient remote control function and the light assembly in response to a non-patient remote control function. In yet another embodiment, the notification system 196 may activate the vibrating device in response to the patient remote control function and the audible alarm device in response to a non-patient remote control function. In another embodiment, the notification system 196 may activate multiple modalities, such as the electronic display and the vibrating device, in response to the patient remote control function, while activating just one modality in response to a non-patient remote control function.

The notification generated during step 303 of the method may also vary from one patient remote control function to another. For example, in an embodiment where the patient remote control function causes the actuators 121, 122 to lift the patient support deck 140, the notification system 196 may first illuminate a light assembly to alert persons within the vicinity of the patient support apparatus 100 to maintain a safe distance from the patient support apparatus. In contrast, in an embodiment where the patient remote control function causes the actuators 121, 122 to incline one or more portions of the patient support deck 140, the notification system 196 may first activate an electronic display, advising the patient to lean back in a relaxed position.

Similarly, the notification generated during step 303 of the method may vary from one non-patient remote control function to another. For example, in an embodiment where the non-patient remote control function causes the controller 195 to activate the speaker of the patient support apparatus 100, the notification system 196 may first illuminate the green validation light. In contrast, in an embodiment where the non-patient remote control function causes the controller 195 to activate a scale of the patient support apparatus to weigh the patient, the notification system 196 may first activate the electronic display to indicate that the patient will be weighed and for the patient to lie still.

Furthermore, the notification generated during step 303 may be based on medical procedure data. In such an embodiment, the medical procedure data may include a type of medical procedure undergone by the patient, a duration since a last medical procedure undergone by the patient, a duration since admittance of the patient to a caregiving facility, or combinations thereof. For example, in an embodiment where the selected remote control function 221 causes the actuators 121, 122 to lift the patient support deck 140, the notification system 196 may first activate the electronic display to inform the caregiver that the patient has recently undergone a surgical procedure.

The notification generated during step 303 may also be based on patient characteristic data. In such an embodiment, the patient characteristic data may include a height of the patient, fall risk data, width of the patient, age of the patient, weight of the patient, body mass index of the patient, or combinations thereof. For instance, in an embodiment where the selected remote control function 221 causes the actuators 121, 122 to lower one of the side rails 171, 172, 173, 174, the notification system 196 may first illuminate the light assembly of red warning lights if the patient has a high fall risk based on the fall risk data.

The notification generated during step 303 may also be based on caregiver observation data. In such an embodiment, the caregiver observation data may include psychological data of the patient, phobia data of the patient, pain sensitivity data of the patient, nausea data of the patient, or combinations thereof. In an example embodiment where the selected remote control function 221 causes the actuators 121, 122 to lift the patient support deck 140, the notification system 196 may first activate the electronic display to inform the caregiver that the patient has a fear of heights based on the phobia data.

The notification generated during step 303 may also be based on a state of the patient support apparatus. In such an embodiment, the state of the patient support apparatus 100 may include a height of a component of the patient support apparatus 100, a length of a component of the patient support apparatus 100, a position of a component of the patient support apparatus 100, a state of a component of the patient support apparatus 100, a velocity of a component of the patient support apparatus 100, or an acceleration of a component of the patient support apparatus 100. For example, in an embodiment where the selected remote control function 221 causes the actuators 121, 122 to incline the back section of the patient support deck 140, the notification system 196 may first illuminate the light assembly of red warning lights if the brake of the patient support apparatus 100 is not applied. As another example, in an embodiment where the selected remote control function 221 causes the actuators 121, 122 to turn the patient, the notification system 196 may first activate the audible alarm device if any one of the side rails 171, 172, 173, 174 are in a lowered position.

The notification generated during step 303 may also be based on a patient condition. In such an embodiment, the controller 195 may receive the patient condition from an electronic medical record. In a further embodiment, the controller 195 may determine a movement sensitivity score based on the patient condition and generate the notification based on the movement sensitivity score. For example, in an embodiment where the patient is suffering from a vestibular disorder or from myalgia, according to the electronic medical record, the controller 195 may determine that the patient has a high movement sensitivity score. Accordingly, if the selected remote control function 221 causes the actuators 121, 122 to lift the patient support deck 140, the notification system 196 may first activate the electronic display to inform the caregiver that the patient is sensitive to movement.

The notification generated during step 303 may also be based on medication data and/or prior injury data. For example, in an embodiment where the selected remote control function 221 causes the actuators 121, 122 to lift the patient support deck 140, the notification system 196 may first activate the electronic display to indicate that the patient has recently ingested a medication that may induce nausea based on the medication data. Similarly, in an embodiment where the selected remote control function 221 causes the actuators 121, 122 to lift the foot section (i.e. the foot end) of the patient support deck 140, the notification system 196 may first activate the electronic display to indicate that the patient has recently broken their leg based on the prior injury data.

It should be noted that the notification may be generated during 303 based on a combination of the medical procedure data, the patient characteristic data, the caregiver observation data, the patient condition, the state of the patient support apparatus 100, the medication data, and the prior injury data. As such, the example embodiments discussed above may be combined. For example, in an embodiment where the selected remote control function causes the actuators 121, 122 to lift the patient support deck 140, the notification system 196 may first activate the electronic display to inform the caregiver that the patient has a fear of heights based on the phobia data and that the patient has recently ingested a medication that may induce nausea based on the medication data.

Similarly, the output signal in step 305 may be transmitted based on the medical procedure data, the patient characteristic data, the caregiver observation data, the patient condition, the state of the patient support apparatus 100, the medication data, the prior injury data, or combinations thereof. In other words, the controller 195 may incorporate the above discussed data, states, and conditions when instructing the actuators 121, 122 to execute the selected remote control function 221.

The controller 195 may receive and store the medical procedure data, the patient characteristic data, the patient condition, the state of the patient support apparatus, the medication data, and the prior injury data in a variety of ways. For example, the caregiver or the patient may manually supply the above data, states, and conditions to the controller 195. In such an embodiment, the data, states, and conditions may be stored locally in the memory 240 as data and/or instructions readable by the controller 195. In other embodiments, the caregiver or the patient may supply the data, states, and conditions to the controller 195 via the remote device 199. In still other embodiments, the controller 195 may receive and store the data, states, and conditions using an external memory storage device or a cloud storage service. In this way, the controller 195 may receive, store, and, therefore, generate the notification and transmit the output signal to the actuators 121, 122 based on the data, states, and conditions.

As previously stated, step 304 of the method occurs prior to step 305. In other words, persons within the vicinity of the patient support apparatus 100 may be notified of the selected remote control function 221 by the notification system 196 prior to its execution. To further characterize this relationship, step 304 can be described as occurring at a first time that is prior to a second time at which step 305 occurs. The first and second time may be defined as a specific time stamps. For example, in one embodiment, the first time may be defined as 12:01 PM and the second time may be defined as 12:03 PM. The first and second time may also be defined as an amount of time relative to one another. For example, the first time may be defined as 5 minutes before the second time. Similarly, the second time may be defined as 30 seconds after the first time. It should be noted that any suitable time or amount of time may be used for the first and second time.

The first time and second time may be based on the selected remote control function 221. In some embodiments, the first time may vary between patient remote control functions and non-patient remote control functions. For example, the first time and second time may vary between a patient remote control function that causes the actuators 121, 122 to move the patient support deck 140 into an emergency mode, such as CPR mode, and a non-patient remote control function that causes the controller 195 to activate the scale of the patient support apparatus 100 weigh the patient. In the embodiment where the patient remote control function causes the actuators 121, 122 to move the patient support deck 140 into CPR mode, it may be desirable to move the patient support deck 140 as quickly as possible. Therefore, the notification system 196 may execute the notification at a first time that is immediately prior to a second time when the controller 195 transmits the output signal to the actuators 121, 122 to move the patient support deck 140. In contrast, in the embodiment where the non-patient remote control function causes the controller 195 to activate the scale of the patient support apparatus 100, it may be desirable to allow some time for the patient to lie still. Therefore, the notification system 196 may activate the electronic display at a first time to indicate that the patient will be weighed and for the patient to lie still. The controller 195 may then activate the scale at a second time 10 seconds later, allowing the patient to lie still before they are weighed.

In another embodiment, the first time and the second time may be based on the medical procedure data, the patient characteristic data, the caregiver observation data, the patient condition, the state of the patient support apparatus, the medication data, the prior injury data, or combinations thereof. For instance, in an embodiment where the selected remote control function 221 causes actuators 121, 122 to lift the foot section of the patient support deck 140 and the patient has recently suffered a leg injury based on the patient condition data, the notification system 196 may execute the notification at a first time that allows the caregiver to secure the patient's leg before the foot section is lifted. For example, the notification system 196 may activate the electronic display at a first time to indicate that the foot section will be lifted and to notify the caregiver to secure the patient's leg. The controller 195 may then transmit the output signal to the actuators 121, 122 at a second time, such as 30 seconds later, allowing the caregiver to secure the patient's leg prior to moving the foot section.

By performing step 304 before step 305, the method provides a variety of advantages. One such advantage is that the notification may aid in preventatively lowering an anxiety of persons within the vicinity of the patient support apparatus 100. For example, in an embodiment where the selected remote control function 221 causes the actuators 121, 122 to lift the patient support deck 140, the notifications system 195 may first activate the light assembly of red warning lights to warn persons near the patient support apparatus 100 that the patient support deck 140 will be lifted. In this way, persons within the vicinity of the patient support apparatus 100, such as the patients themselves, may be less surprised and demonstrate a lower level of anxiety when the actuators 121, 122 begin lifting the patient support deck 140.

Another advantage is that the notification may inform persons within the vicinity of the patient support apparatus 100 of proper safety procedures concerning the selected remote control function 221. For example, the notification system 196 may activate the electronic display to warn the patient to grab a side rail 171, 172, 173, 174 prior to the actuators 121, 122 lifting the patient support deck 140. In another example, the notification system 196 may activate the electronic display to warn the caregiver to ensure that the patient is properly fastened prior to lifting the patient support deck 140. In yet another example, the notification may activate the electronic display to warn persons not disposed on the patient support structure 110 to maintain a safe distance from the patient support deck prior to execution of the selected remote control function 221. In this way, the notification promotes proper safety procedures in persons within the vicinity of the patient support apparatus 100.

Of course, it is to be appreciated that advantages and examples not specifically discussed above may arise from the method and the patient support apparatus 100. The above embodiments discuss example selected remote control functions 221, example notifications, and example advantages of the method and patient support apparatus 100 and should thus not be construed as limiting.

As previously stated, the patient support apparatus 100 may also include the sensing system 197. Referring back to FIG. 2, the controller 195 may be coupled to the sensing system 197 and the controller 195 may receive a sensor input signal from the sensing system 197. The sensing system 197, as shown in FIG. 2, includes at least one sensor 210.

The sensing system 197 provides the sensor input signal to the controller 195. For instance, the sensing system 197 may provide the sensor input signal based on sensing the patient condition and/or the state of the patient support apparatus 100 with the sensor 210. Accordingly, the controller 195 may generate the notification and transmit the output signal to the actuators 121, 122 based on the sensed patient condition and/or the sensed state of the patient support apparatus 100. The sensor input signal provided by the sensing system 197 may include a patient condition sensor input signal representing the sensed patient condition of the patient and/or a patient support apparatus sensor input signal representing the sensed state of the patient support apparatus 100.

The patient condition sensor input signal may further include a patient physiological sensor input signal and/or a patient presence sensor input signal. The patient physiological sensor input signal may be provided by a patient physiological sensor and the patient presence sensor input signal may be provided by a patient presence sensor. The patient physiological sensor determines a physiological state of the patient and the patient presence sensor determines a presence of the patient, or, in other words, whether the patient is disposed on or adjacent to the patient support apparatus 100. In such embodiments, the at least one sensor 210 may include the patient physiological sensor and the patient presence sensor.

To determine the physiological state of the patient, the patient physiological sensor may include a heart rate sensor, a patient temperature sensor, a moisture sensor, a shear sensor, a neurological sensor, a load cell, a blood pressure sensor, a camera, a force sensor, a breathing monitor, a patient expression sensor, a patient acoustic sensor, or combinations thereof. The patient presence sensor may include a force sensor, a load cell, a motion sensor, a switch, an optical sensor, an infrared sensor, an electromagnetic sensor, an accelerometer, a potentiometer, an ultrasonic sensor, or combinations thereof for determining the presence of the patient.

To determine the sensed state of the patient support apparatus 100, the at least one sensor 210 of the sensing system 197 may determine the height of a component of the patient support apparatus 100, the length of a component of the patient support apparatus 100, the position of a component of the patient support apparatus 100, the state of a component of the patient support apparatus 100, the velocity of a component of the patient support apparatus 100, and/or the acceleration of a component of the patient support apparatus 100.

As previously stated, the patient support apparatus 100 may include the local user interface 198 for receiving a local override from persons within the vicinity of the patient support apparatus 100. Referring to FIG. 2, the controller 195 may be coupled to the local user interface 198 and the controller 195 may receive a local override signal 223.

As such, the controller 195 may transmit the output signal to the actuators 121, 122 based on the local user interface signal 223. For example, in one embodiment, the selected remote control instructs the controller 195 to lift the patient support deck 140. Accordingly, the controller 195 transmits the corresponding output signal to the actuators 121, 122. In such an embodiment, if the local user interface 198 is configured to receive the local override from persons within the vicinity of the patient support apparatus 100, the local user interface 198 transmits the local override signal 223 to the controller 195. The controller 195 then ceases transmission of the output signal to the actuators 121, 122, terminating movement of the patient support deck 140.

As shown in FIG. 2, in some embodiments, the remote control function 221 may be further defined as a patient therapy protocol 222. As previously discussed, the remote control function 221 may be categorized as a non-patient remote control function or a patient remote control function. The patient remote control function may be further categorized as a discrete patient remote control function or a periodic patient remote control function. As used herein, a discrete patient remote control function causes the controller 195 to execute a singular command. For example, a discrete patient remote control function may cause the actuators 121, 122 to lift the patient support deck 140 or to incline the back section of the patient support deck 140. As used herein, a periodic patient remote control function causes the controller 195 to execute a singular command periodically. For example, a periodic patient remote control function may cause the actuators 121, 122 to incline the back section of the patient support deck 140 prior to a specified breakfast time, lunch time, and dinner time. In another example, a periodic patient remote control function may cause the actuators 121, 122 to elevate a foot section of the patient support deck 140 every hour. The patient therapy protocol 222 is an example of a periodic patient remote control function. In one embodiment of the patient therapy protocol 222, the patient therapy protocol 222 may cause the actuators 121, 122 to turn the patient every half hour to reduce a risk of acquiring pressure ulcers.

Figure 4:
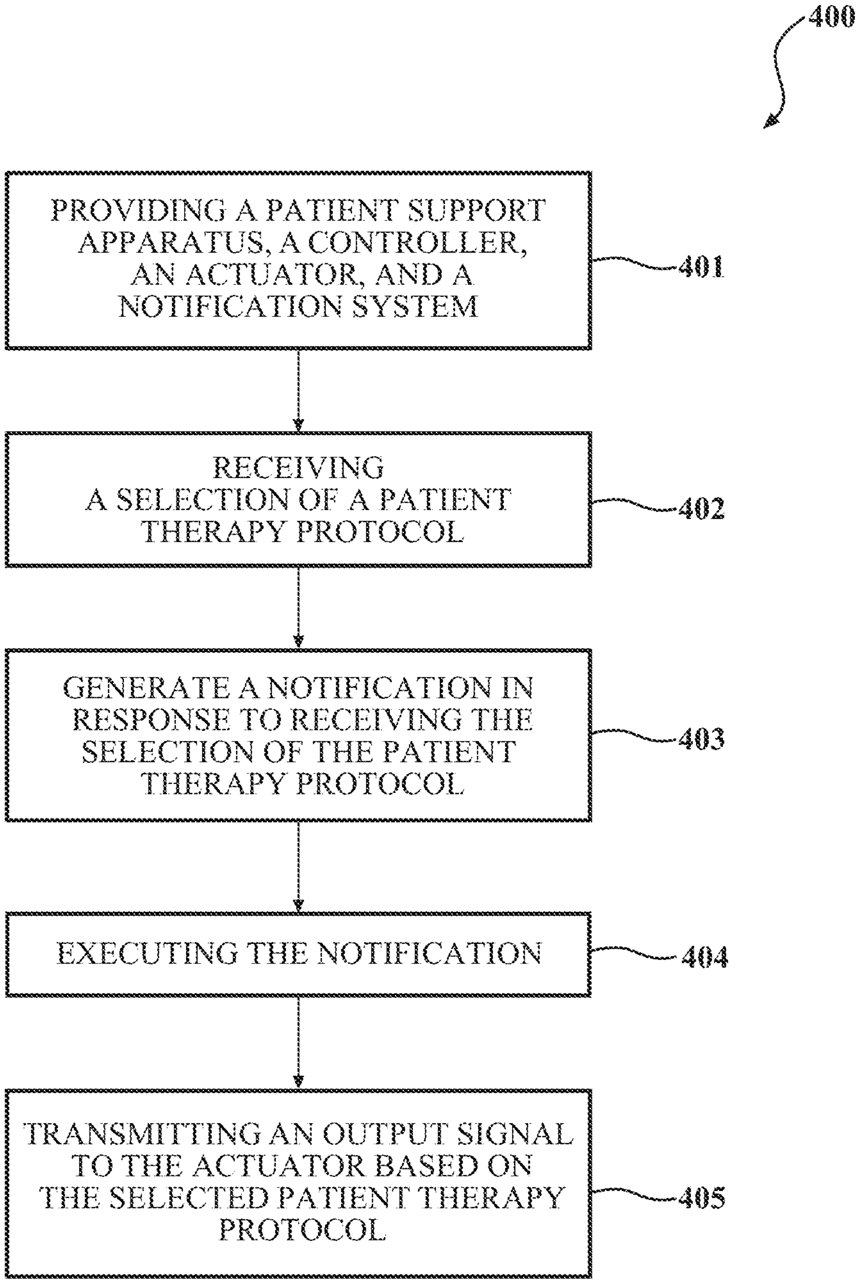
FIG. 4 is a flowchart illustrating a method of notifying persons within the vicinity of the patient support apparatus of a selected patient therapy protocol.

FIG. 4 provides a flowchart illustrating a method of notifying persons within the vicinity of the patient support apparatus 100 of the selected patient therapy protocol 222. As shown, the method includes a step 401 of providing the patient support apparatus 100, the controller 195, the actuator 121, and the notification system 196. The method also includes a step 402 of receiving a selection of the patient therapy protocol 222 via the communication network; a step 403 of generating the notification in response to receiving the selection of the patient therapy protocol; a step 404 of executing the notification; and a step 405 of transmitting the output signal to the actuators 121, 122 based on the selected patient therapy protocol 222. It should be noted that step 404 occurs prior to step 405. As such, persons within the vicinity of the patient support apparatus 100 may be notified of the selected patient therapy protocol 222 prior to its execution.

Additionally, it should be noted that the method shown in FIG. 4 may be cyclical in nature. That is, the method may repeat steps 403, 404, and 405 based on the patient therapy protocol 222. As previously stated, the patient therapy protocol 222 may be defined as a periodic patient remote control function where a singular command is executed periodically. As such, the notification may be generated and executed each time the singular command is to be executed. Similarly, the output signal is transmitted to the actuators 121, 122 each time the singular command is to be executed.

An example embodiment where the patient therapy protocol 222 causes the actuators 121, 122 to turn the patient every half hour for twelve total hours further illustrates the cyclical nature of the method. In such an embodiment, the controller 195 may receive the patient therapy protocol 222 via the communication network and generates the notification in response. The notification system 196 then executes the notification. For example, the notification system 196 may illuminate a light assembly of yellow lights indicating that the patient will be turned. Then, the controller 195 transmits the output signal to the actuators 121, 122 to turn the patient. After a half hour, the controller 195 again generates the notification, the notification system 196 again executes the notification, and the controller 195 again transmits the output signal to the actuators 121, 122 to turn the patient. This process continues for a total of twelve hours. It should be noted that, while the actuators 121, 122 in the above example embodiment turn the patient every half hour for twelve total hours, the actuators 121, 122 may turn the patient at any suitable interval of time for any suitable total amount of time.

Figure 5:
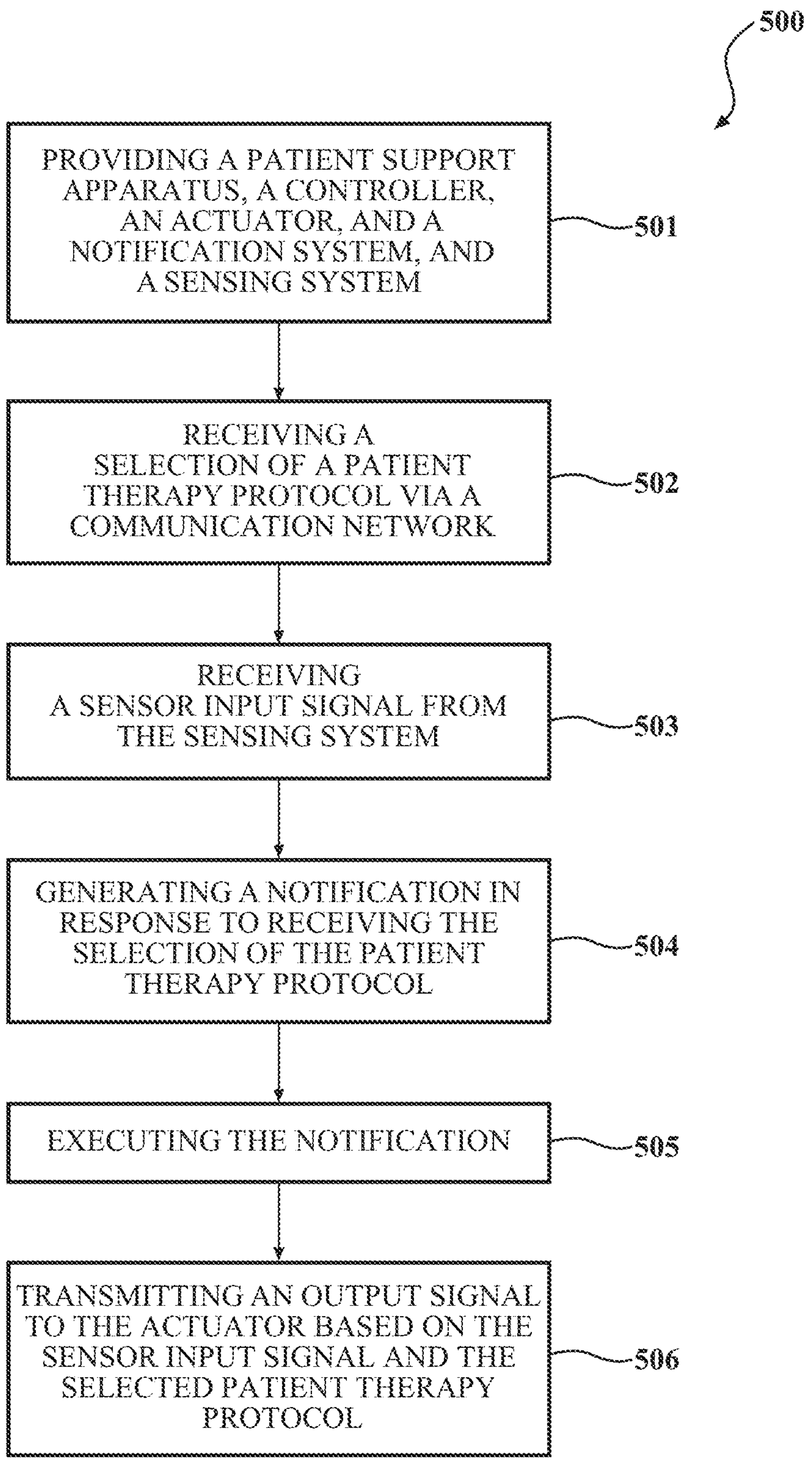
FIG. 5 is a flowchart illustrating a method of receiving a sensor input signal from the sensing system and notifying persons within the vicinity of the patient support apparatus of a selected patient therapy protocol.

In a further embodiment of the patient support apparatus 100, the remote control function 221 may be further defined as a patient therapy protocol 222 and the patient support apparatus 100 may include the sensing system 197. FIG. 5 provides a flowchart illustrating a method of receiving the sensor input signal from the sensing system 197 and notifying persons within the vicinity of the patient support apparatus 100 of the selected patient therapy protocol 222. As shown, the method 500 includes a step 501 of providing the patient support apparatus 100, the controller 195, the actuator 121, the notification system 196, and the sensing system 197. The method 500 also includes a step 502 of receiving the selection of the patient therapy protocol 222 via the communication network; a step 503 of receiving the sensor input signal from the sensing system 197; a step 504 of generating the notification in response to receiving the selection of the patient therapy protocol; a step 505 of executing the notification; and a step 506 of transmitting the output signal to the actuators 121, 122 based on the sensor input signal and the patient therapy protocol 222. It should be noted that steps 503 and 505 occur prior to step 506. As such, the controller 195 receives the sensor input from the sensing system 197 and persons within the vicinity of the patient support apparatus 100 are notified of the selected patient therapy protocol 222 prior to the controller 195 executing the selected patient therapy protocol 222.

Additionally, it should be noted that the method 500 may be cyclical in nature. That is, the method may repeat steps 503, 504, 505, and 506. As previously stated, the patient therapy protocol 222 may be defined as a periodic patient remote control function where a singular command is executed periodically. As such, the notification may be generated and executed each time the singular command is to be executed. Similarly, the sensor input signal may be received each time the singular command is to be executed. Accordingly, the output signal is transmitted to the actuators 121, 122 each time the singular command is to be executed.

An example embodiment where the patient therapy protocol 222 causes the actuators 121, 122 to turn the patient based on a Braden Scale score, which predicts pressure ulcer risk, further illustrates the cyclical nature of the method. In the example embodiment, the controller 195 receives a selection of the patient therapy protocol via the communication network. The controller 195 then receives the sensor input signal from the sensing system 197. In the example embodiment, the sensor input signal may indicate a moisture level of the patient support apparatus 100, an activity level of the patient, and/or a friction measurement between the patient and the patient support apparatus 100. After receiving the sensor input signal, the controller 195 may calculate the Braden Scale score of the patient. If the calculated Braden Scale score exceeds a threshold, the controller 195 generates the notification and the notification system 196 executes the notification. For example, the notification system 196 may illuminate the light assembly of yellow lights to indicate that the patient will be turned. Afterwards, the controller 195 transmits the output signal to the actuators 121, 122 to turn the patient. Thereafter, the controller 195 continually receives the sensor input signal and continually calculates the Braden Scale score of the patient. If the calculated Braden Scale score again exceeds the threshold, the controller 195 again generates the notification, the notification system 196 again executes the notification, and the controller 195 again transmits the output signal to turn the patient.

As previously discussed, the controller 195 may preventatively lower an anxiety of persons within the vicinity of the patient support apparatus 100 by activating the notification system 196 to generate the notification before implementing the patient therapy protocol 222. Similarly, in the previously described example embodiment, the controller 100 is able to lower the anxiety of such persons by receiving the sensor input signal from the sensing system 197 and dynamically adjusting the patient therapy protocol 222. Therefore, through inclusion of the sensing system 197 and the notification system 196, the patient support apparatus 100 and the methods described above offer many approaches to advantageously lowering the anxiety of persons within the vicinity of the patient support apparatus 100. Furthermore, it should be appreciated that the teachings, advantages, and examples from previously discussed methods and configurations of the controller 195 may also apply to the method shown in FIG. 4 and/or the method shown in FIG. 5.

It should be understood that, while embodiments discussed herein describe techniques for notifying persons of a remote control function 221 of the patient support apparatus 100, the techniques may be used for notifying persons a remote control function 211 of other medical devices. For instance, these medical devices may include equipment such as lights, televisions, temperature management systems, respirators, IV lines, heart rate monitors, surgical tools, or any other devices that may be used in medical procedures or in the provision of medical services to patients. Therefore, the techniques for notifying persons of a remote control function 221 may apply to any of the above-described medical devices, or any other medical device that may be used in medical procedures or in the provision of medical services to patients.

It will be further appreciated that the terms “include,” “includes,” and “including” have the same meaning as the terms “comprise,” “comprises,” and “comprising.” Moreover, it will be appreciated that terms such as “first,” “second,” “third,” and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention is intended to be defined in the independent claims, with specific features laid out in the dependent claims, wherein the subject-matter of a claim dependent from one independent claim can also be implemented in connection with another independent claim.

The invention claimed is:

1. A system for facilitating care of a patient, the system comprising:
- a communication network;
- a patient therapy device coupled to the communication network and being actuatable to provide therapy treatment to the patient;
- a patient support apparatus including:
  - a patient support structure configured to support the patient, a controller coupled to the communication network and configured to:

receive a selection of a remote control function requiring the patient therapy device to actuate;

generate a notification in response to receiving the selection of the remote control function; and transmit an output signal to the patient therapy device based on the selection of the remote control function, and a notification system configured to execute the notification to notify a person within a vicinity of the patient support structure at a first time, the first time being after receiving the selection of the remote control function and prior to transmitting, with the controller, the output signal to the patient therapy device based on the selection of the remote control function.

2. The system of claim 1, wherein the patient therapy device includes a vibration therapy device, a percussion therapy device, a compression therapy device, a patient warming device, an electrical stimulation device, or combinations thereof.

3. The system of claim 1, wherein the patient therapy device is configured to at least partially move the patient via vibration, percussion, compression, electrical stimulation, or combinations thereof.

4. The system of claim 1, wherein the controller is further configured to generate the notification based on medical procedure data, patient characteristic data, caregiver observation data, a state of the patient support apparatus, a patient condition of the patient, medication data, prior injury data, or combinations thereof.

5. The system of claim 1, wherein the controller is further configured to generate the notification based on medical procedure data; and wherein the medical procedure data comprises a type of medical procedure undergone by the patient, a duration since a last medical procedure undergone by the patient, a duration since admittance of the patient to a caregiving facility, or combinations thereof.

6. The system of claim 1, wherein the controller is configured to generate the notification based on patient characteristic data; and wherein the patient characteristic data comprises height of the patient, fall risk data, width of the patient, age of the patient, weight of the patient, body mass index of the patient, or combinations thereof.

7. The system of claim 1, wherein the controller is configured to generate the notification based on caregiver observation data; and wherein the caregiver observation data comprises psychological data of the patient, phobia data of the patient, pain sensitivity data of the patient, nausea data of the patient, or combinations thereof.

8. The system of claim 1, wherein the controller is configured to generate the notification based on a state of the patient support apparatus; and wherein the state of the patient support apparatus comprises a height of a component of the patient support apparatus, a length of a component of the patient support apparatus, a position of a component of the patient support apparatus, a state of a component of the patient support apparatus, a velocity of a component of the patient support apparatus, or an acceleration of a component of the patient support apparatus.

9. The system of claim 1, wherein the controller is configured to generate the notification based on a patient condition; and wherein the controller is configured to receive the patient condition from an electronic medical record.

10. The system of claim 1, wherein the controller is configured to generate the notification based on a patient condition; and wherein the controller is further configured to determine a movement sensitivity score based on the patient condition and to generate the notification based on the movement sensitivity score.

11. The system of claim 1, wherein the patient support apparatus includes a sensing system coupled to the controller, the sensing system being configured to provide a sensor input signal to the controller, and wherein the controller is configured to generate the notification based on the sensor input signal.

12. The system of claim 11, wherein the sensing system is configured to provide the sensor input signal to the controller based on sensing at least one of a patient condition and a state of the patient support apparatus.

13. The system of claim 12, wherein the sensing system is configured to sense the patient condition and wherein the sensor input signal comprises a patient condition sensor input signal representing a sensed patient condition of the patient.

14. The system of claim 13, wherein the sensing system comprises a patient physiological sensor coupled to the controller, the patient physiological sensor configured to determine a physiological state of the patient; and wherein the patient condition sensor input signal comprises a physiological sensor input signal generated by the patient physiological sensor and representing the determined physiological state of the patient.

15. The system of claim 13, wherein the sensing system comprises a patient presence sensor coupled to the controller, the patient presence sensor configured to determine whether the patient is disposed adjacent to the patient support structure;

wherein the patient condition sensor input signal comprises a patient presence sensor input signal generated by the patient presence sensor; and wherein the patient presence sensor comprises an optical sensor, an infrared sensor, or combinations thereof.

16. The system of claim 11, wherein the remote control function comprises a patient therapy protocol, wherein the controller is configured to:

receive the sensor input signal from the sensing system prior to transmitting the output signal to the patient therapy device;

generate the notification in response to receiving a selection of the patient therapy protocol; and transmit the output signal to the patient therapy device based on the sensor input signal and the patient therapy protocol.

17. The system of claim 1, wherein the controller determines the first time based on the selection of the remote control function.

18. The system of claim 1, wherein the controller is configured to determine the first time based on medical procedure data, patient characteristic data, caregiver observation data, a patient condition of the patient, a state of the patient support apparatus, medication data, prior injury data, or combinations thereof.

19. The system of claim 1, wherein the controller is further configured to transmit the output signal to the patient therapy device based on medical procedure data, patient characteristic data, caregiver observation data, a patient condition of the patient, a state of the patient support apparatus, medication data, prior injury data, or combinations thereof.

20. The system of claim 1, wherein the notification system comprises a visual alert system, an audio alert system, a tactile alert system, or combinations thereof.

* * * * *